United States Patent [19]

Hayhurst et al.

[11] Patent Number: 5,037,422

[45] Date of Patent: Aug. 6, 1991

[54] BONE ANCHOR AND METHOD OF ANCHORING A SUTURE TO A BONE

[75] Inventors: John O. Hayhurst, Milwaukie, Oreg.; Alan A. Small, Needham; Jeffrey C. Cerier, Franklin, both of Mass.

[73] Assignee: Acufex Microsurgical, Inc., Mansfield, Mass.

[21] Appl. No.: 547,783

[22] Filed: Jul. 2, 1990

[51] Int. Cl.$^5$ .............................................. A61B 17/00
[52] U.S. Cl. ...................................... 606/72; 606/74; 606/75; 606/232; 411/511
[58] Field of Search ...................................... 606/72–75, 606/220, 232; 411/340, 508, 509, 510, 511, 904

[56] References Cited

U.S. PATENT DOCUMENTS

| | | | |
|---|---|---|---|
| 4,013,071 | 3/1977 | Rosenberg | 606/73 |
| 4,409,974 | 10/1983 | Freeland | 606/232 |
| 4,738,255 | 4/1988 | Goble et al. | 606/232 |
| 4,741,330 | 5/1988 | Hayhurst et al. | 606/86 |

Primary Examiner—Stephen C. Pellegrino
Assistant Examiner—Gary Jackson
Attorney, Agent, or Firm—Brooks & Kushman

[57] ABSTRACT

A bone anchor (10) for securing a suture to a bone (38). The bone anchor (10) has a tip (16) at its distal end (18) and at least one resilient wall (27) extending to a trailing end (20) of the body (12) of the anchor. The wall (27) has a ridge (14), or barb, formed on an outer surface. The ridge (14) defines an edge (34) that digs into a hole (36) in the bone (38) in which it is positioned. A strand of suturing thread (22) extends through a suture receiving opening (24) in the tip (16) of the anchor. When tension is applied to the suturing thread (22), it causes the ridge (14) to dig into the walls of the hole (36) in the bone (38). Two resilient walls (27,28) are preferably provided which include an annular ridge-shaped barb (14). The two resilient walls 27, 28 scissor outwardly upon application of tension to the suturing thread. The tip (16) is generally frustoconical with a rounded leading end. The method of the present invention employs the suture anchor (10) and includes the steps of forming a hole (36) in a bone (38), inserting the suture anchor (10) to a desired depth in the hole (36) in the bone (38) with the tip (16) inserted first and the trailing resilient walls (27,28) following the tip. Suturing thread (22) extends from the suture receiving opening (24) in the tip and along the length of the walls (27,28) out of the hole (36) in the bone (38). The next step is to pull on a portion of the suturing thread extending out of the bone (38) to urge the barb (14) into firmer engagement with the bore hole (36).

26 Claims, 1 Drawing Sheet

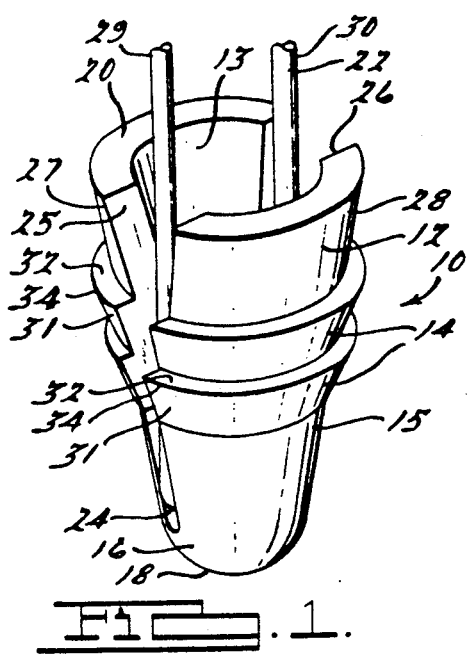
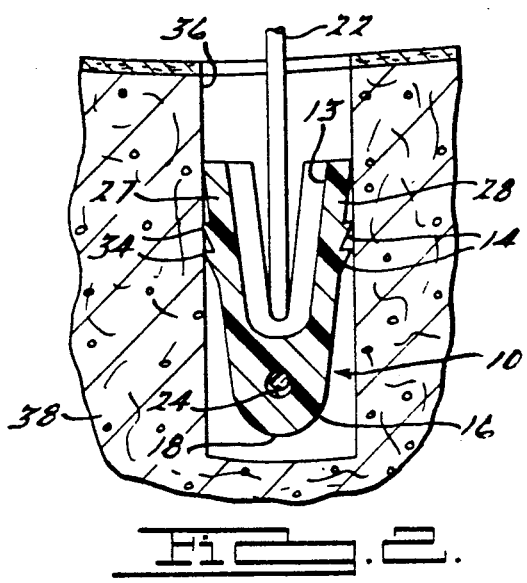
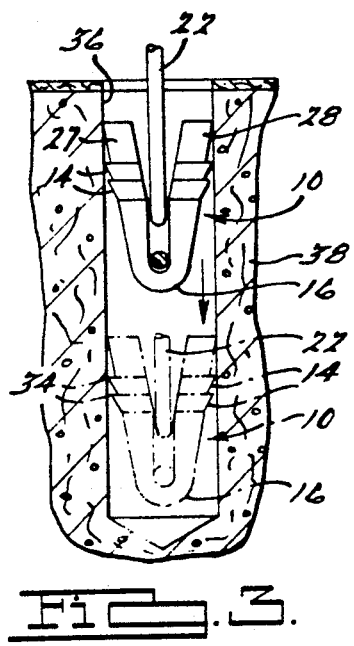
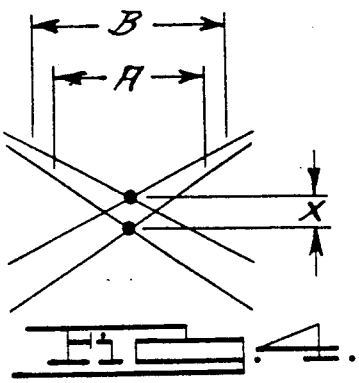
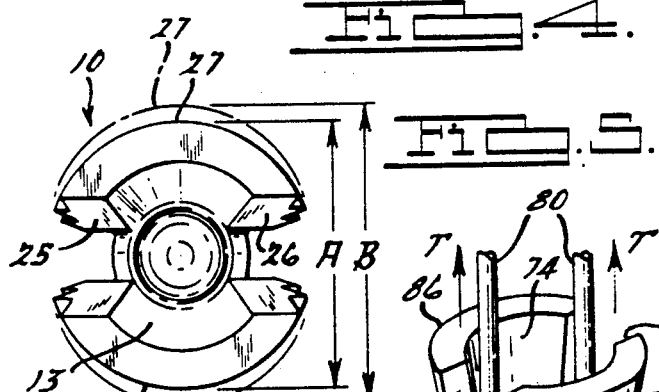
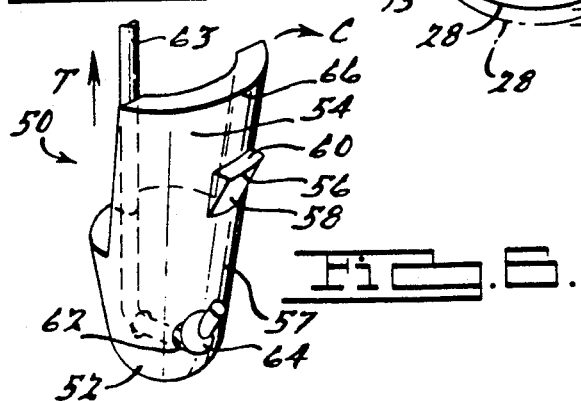
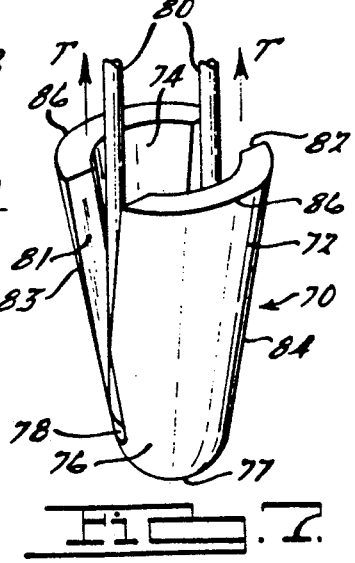

BONE ANCHOR AND METHOD OF ANCHORING A SUTURE TO A BONE

TECHNICAL FIELD

The present invention relates to anchors for surgical sutures, and more particularly relates to bone anchors which are inserted into a hole formed in a bone by a drilling operation.

BACKGROUND ART

Suture anchors used to secure sutures in openings formed in bones are important for joint reconstructive surgery and arthroscopic surgical techniques. Such suture anchors are used, for instance, to anchor ligaments or tendons to bones in knee, shoulder and elbow reconstruction and repair operations.

Important attributes of bone anchors are that they be easy to insert, and provide a firm anchor. Bone anchors also should be simple and reliable. Bone anchors may be bio-absorbable or nonbio-absorbable depending upon the material used to form the bone anchor. Either can be used depending on the type of operation and selection of the surgeon.

Initially, one type of bone anchor took the form of a fish hook-type barb which was inserted into a hole and hooked into the soft marrow of the bone. Another prior approach to suture anchors is disclosed in U.S. Pat. No. 4,738,255 to Goble, et al. This patent discloses a suture anchor delivery system which uses a specialized two-piece anchor including an anchor rivet and a slotted ring. The anchor rivet is drawn into the slotted ring to deform the slotted ring into an acorn-shape when pressure is applied by an anchor mandrel through which the suture is drawn. This slotted ring includes slots that are split to allow the ring to be deformed and an anchor ridge is formed around the inside circumference of the slotted ring. As compared with the present invention, the Goble suture anchor is more complex in configuration and requires a specialized anchor delivery system for manipulating the two-piece rivet and slotted ring. Also, manufacture of the Goble suture anchor requires close tolerance assembly of the two-piece anchor and cooperation between the two parts of the anchor.

Another patent disclosing a system for fastening articles to bones is disclosed in U.S. Pat. No. 4,013,071 to Rosenberg. This patent discloses an orthopedic screw with an expandable portion including side slits which are formed radially through the distal end of a screw. The side slits produce a plurality of outwardly expansible tips that are flared by driving a rod-shape member through an internal bore of the orthopedic screw. The Rosenberg device is turned in a manner of a screw for insertion which presents some difficulties in performing arthroscopic procedures. Further, the Rosenberg device requires close tolerance in manufacturing and assembly.

Still another prior art system is shown in U.S. Pat. No. 4,741,330 to Hayhurst. This patent discloses anchoring devices for attaching sutures to bones, the anchoring devices being deformable cylindrical shaped solid plugs attached at their midpoints to sutures.

A primary objective of the present invention is to provide a bone anchor which is inexpensive to manufacture and simple to install.

Another object of the invention is to provide a bone anchor which automatically locks itself into a bore formed in a bone by simply applying pressure to the suture which causes the barbs or ridges in the bone anchor to dig into the walls of the hole in the bone locking the anchor to the bore hole.

Still another aspect of the present invention is to provide a bone anchor which is compact and automatically guides itself into the hole in the bone.

Another important object of the invention is to provide a bone anchor which may be formed by a simple molding operation with no close tolerance assembly operations required. This feature makes the bone anchor both economical and reliable.

These and other objects are met by the present invention which will become apparent upon review of the following detailed description of the invention in view of the drawings.

DISCLOSURE OF INVENTION

The present invention relates to a bone anchor intended to be used with a suture to secure the suture to a hole formed in a bone. The bone anchor is an elongated thimble-shaped body having a tip at one end of the body. First and second slots extend lengthwise through the elongated body at spaced locations. A suture receiving opening is provided in the tip. At least one ridge, or barb, extends outwardly from the exterior of the elongated body and defines an edge which is adapted to be lodged in the wall of the bore formed in the bone. In one embodiment, a sharp trailing edge comprises the ridge.

The tip of the anchor is its leading end as it is inserted into the bore hole in the bone, and is preferably partially conical in shape and terminates in a rounded end. The conical tip has a rounded end that aides in aligning the anchor with the bore hole in the bone. First and second slots are preferably formed in a substantially cylindrical portion of the anchor and are preferably diametrically opposed. The suture receiving opening in a preferred embodiment extends from the side of the body in which the first slot is formed to the side of the body in which the second slot is formed. The suture is threaded through the suture receiving opening and rearwardly relative to the anchor through the first and second slots and out of the bore hole. A suture trails behind the anchor and out of the bore in the bone so that it is accessible for surgical suturing.

BRIEF DESCRIPTION OF DRAWINGS

FIG. 1 is a perspective view of a bone anchor made in accordance with the present invention.

FIG. 2 is a cross-sectional view showing the bone anchor of the present invention inserted in a hole formed in a bone.

FIG. 3 is a cross-sectional view showing a bone anchor being inserted and then locked into a hole in the bone.

FIG. 4 is a schematic representation showing the scissoring action of the bone anchor when tension is applied after insertion.

FIG. 5 a top plan view showing the bone anchor of the present invention and showing the bone anchor expanded in phantom.

FIG. 6 is a perspective view of an alternative embodiment of the bone anchor of the present invention.

FIG. 7 is a perspective view of another alternative embodiment of the bone anchor of the present invention.

BEST MODE(S) FOR CARRYING OUT THE INVENTION

Referring now to FIG. 1, the bone anchor of the present invention is generally indicated by reference numeral 10. The bone anchor 10 includes a thimble-shaped body 12 which defines an inner cavity 13. A ridge 14, or barb, is formed on the outer surface 15 of the body 12. The ridge is preferably a circular ridge extending about the circumference of the body 12. A tip 16 is formed on the distal end 18 of the body 12. A trailing end 20 of the body 12 is located at the opposite end of the body from the distal end 18. A strand of suture filament 22, or suturing thread, is connected to the body 12 and preferably extends through a suture receiving opening 24 formed through the tip 16 of the body 12.

First and second slots 25 and 26 extend longitudinally through the body 12 from the tip 16 through to the trailing end 20. First and second slots 25 and 26 divide the body 12 into first and second resilient walls 27 and 28. First and second walls 27 and 28 are spaced from each by the first and second slots 25 and 26 and the inner cavity 13. The strand of suture filament 22 extends from the suture receiving opening 24 and is doubled back so that first and second lengths 29 and 30 of the strand extend from the tip 16 through first and second slots 25 and 26, respectively, and extend past the trailing end 20 for use by the surgeon. The first and second lengths of strand 29 and 30 are recessed in the first and second slots 25 and 26 so that the strands do not interfere with the locking action of the ridge 14.

The ridge 14 may be formed as a semi-circular circumferentially extending member. The ridge includes a frustoconical leading surface 31 and a radially extending back surface 32 which intersect to form a relatively sharp edge 34 at the outermost point on the ridge 14. The back surface 32 may be inclined to provide a sharper edge to enhance the ability of the bone anchor 10 to grip the sides of the bore hole 36 in a bone 38.

Referring now to FIGS. 2 through 5, insertion of the bone anchor will be described in greater detail. The bone anchor 10 is inserted into the bore hole 36 formed in the bone 38 by known rotary cutting implements. The tip 16 of the body 12 is preferably rounded and tapered so that it centers itself radially relative to the bore hole 36. As the bone anchor is pushed into the bore hole 36, first and second walls 27 and 28 resiliently converge. The ridge 14 formed on the body 12 preferably has a normal diameter greater than the diameter of the bore hole 36 so that an interference fit is established if the first and second walls 27 and 28 are not pushed together. The bone anchor 10 is pushed into the bore hole 36 by a rigid probe or a specialized insertion tool. When the bone anchor 10 is inserted to the proper depth in the bore hole 36, tension may be applied to the first and second lengths 29 and 30 of the strand 22. Upon application of tension, the edge 34 moves into the sides of the bore hole 36 and grips the bore hole. This causes the first and second resilient walls 27 and 28 to expand outwardly firmly locking the bone anchor in place.

As shown schemmatically in FIG. 4, when tension is applied to the strand 22, the suture receiving opening 24 shown diagrammatically is displaced upwardly a distance X. This upward movement causes the edges 34 to scissor outwardly from an insertion position at a diameter A to an installed position shown by diameter B. Expansion of the bone anchor is shown in FIG. 5 in a top plan view with the bone anchor expanding from a diameter A to a diameter B. Diameter A corresponds to the compressed dimension of the bone anchor while diameter B corresponds to the outwardly scissored dimension or expanded dimension.

The suture receiving opening 24 preferably extends in a line parallel to a line extending through the first and second slots 25 and 26. In this way, the first and second lengths 29 and 30 of the strand 22 may be simply routed from the ends of the suture receiving opening 24 through the first and second slots 25 and 26.

Referring now to FIG. 6, an alternative embodiment of the present invention is generally referred to by reference numeral 50. The bone anchor 50 includes a tip 52 and an arcuate wall 54 which extends rearwardly from the tip 52. A barb 56 is shown on the outer surface 57 of the arcuate wall 54. The barb 56 is formed by a leading ramp surface 58 and a rear facing surface 60. The sharpness of the barb may be varied by changing the angle of the rear facing surface 60. The tip 52 has a suture receiving opening 62. The suture receiving opening 62 is preferably connected to the tip 52 by a knot 64. The suture receiving opening 62 preferably extends from a point below the arcuate wall 54 on the tip 52. The suture receiving opening extends through the tip 52 and rearwardly from the tip. A trailing edge 66 is formed on the opposite end of the bone anchor 50 from the tip. The trailing edge 66 may perform the function of the barb 56 in that it may define an edge that can grip the sides of a bore hole in a bone upon application of tension designated by the letter T on the suture strand 63. When tension T is applied to the suture strand 63, the bone anchor 50 is tipped, or partially rotated, to cause the barb 56 to become lodged in the side of the bore hole. If the barb 56 is not provided, the trailing edge 66 would rotate and could form the anchoring edge in place of the barb 56. The tipping or partial rotation of the bone anchor 50 is shown by arrow C and occurs when tension is applied as denoted by arrow T.

Referring now to FIG. 7, another alternative embodiment of the present invention is generally indicated by reference numeral 70. The bone anchor 70 includes a thimble-shaped body 72 which defines an inner cavity 74. The thimble-shaped body 72 has a tip 76 at its distal end 77. A suture receiving opening 78 extends through the tip 76 to form a passageway through the tip. A strand, or thread, of suture material 80 is threaded through the suture receiving opening 78 and is doubled back through first and second slots 81 and 82. First and second slots 81 and 82 divide the body 72 into first and second resilient walls 83 and 84. The suture material 80 is routed through the first slot 81, then through the suture receiving opening 78 and back through the second slot 82. Both ends of the thread of suture material 80 extend out of the bore hole in a bone when the bone anchor 70 is inserted therein. A relatively sharp trailing edge 86 of the body 72 is located at the opposite end of the body 72 from the distal end 77. The trailing edge 86 forms the barb or ridge that engages the sides of the bore hole. When tension, designated by letter T, is applied to both ends of the thread 80, the trailing edge 86 of the first and second walls 83 and 84 dig into the sides of the bore hole in the bone and are allowed to expand outwardly away from each other to cause the bone anchor 70 to become lodged in the bore hole.

The material used to form the bone anchor may be made of either a bio-absorbable material or a non-absorbable permanent material. Preferred absorbable materials include polyglycolic acid, polylactic acid or trimethylene carbonate copolymers. Preferred non-absorbable materials include acetal homopolymers or copolymers, polyethylene, polypropylene, polyester and copolymers thereof. The suture material may be any conventional type of suture material, such as Ticron, or Dexon brand sutures which are trademarks of Davis & Geck.

The preceding description of the preferred embodiments of the present invention is intended to be illustrative of three preferred forms of the invention. It is anticipated that other modifications and enhancements of the present invention will be apparent based upon the above description. The scope of the present invention should be measured by the following claims, and not limited by the above description of the preferred embodiments.

I claim:

1. A bone anchor for securing a suture to a bore hole in a bone comprising an elongated body having a tip at a distal end of the body, first and second slots extending lengthwise at spaced locations on the body, a suture receiving opening extending through the tip, and at least one ridge extending outwardly from the exterior of the body and defining an edge adapted to lodge in the wall of the bore hole.

2. The bone anchor of claim 1 wherein said tip is partially conical and terminates in a rounded end.

3. The bone anchor of claim 1 wherein the body includes a substantially cylindrical portion, the first and second slots are diametrically opposed and the suture receiving opening extends from the side of the body in which the first slot is formed to the side of the body in which the second slot is formed.

4. The bone anchor of claim 1 wherein a plurality of ridges are provided.

5. The bone anchor of claim 1 wherein said ridge is generally circular and extends about the circumference of the cylindrical portion and is interrupted by the first and second slots.

6. The bone anchor of claim 5 wherein said ridge has a frustoconical leading surface with a minimum diameter closest the distal end of the body and a radially extending back surface facing away from the distal end which forms an edge with the leading surface that digs into the wall of the bore hole to lock the anchor in the bore hole.

7. A bone anchor and a suture in combination for securing a suture to a hole formed in a bone, the bore having a wall comprising:
an elongated body having a tip at a distal end, first and second slots extending lengthwise in said body at circumferentially spaced locations in the body, said tip having a suture receiving opening extending diametrically through the tip, and at least one ridge extending outwardly from the exterior of the body and defining an edge adapted to lodge in the wall of the hole formed in the bone; and
a strand of suture filament extending through the suture receiving opening in the tip and through first and second slots and out of the hole wherein said body is inserted into the hole with the tip entering the hole first and two ends of the strand extending from the hole whereby tension may be applied to the two ends of the strand exerting an outward force on the body causing said ridge to become lodged securely in the wall of the hole formed in the bone.

8. The combination of claim 7 wherein said tip is partially conical and terminates in a rounded end.

9. The combination of claim 7 wherein the first and second slots are diametrically opposed and the suture receiving opening extends from the side of the body in which the first slot is formed to the side of the body in which the second slot is formed.

10. The combination of claim 7 wherein a plurality of ridges are provided.

11. The combination of claim 7 wherein said ridge is generally circular and extends about the circumference of the cylindrical portion and is interrupted by the first and second slots.

12. The combination of claim 11 wherein said ridge has a frustoconical leading surface with a minimum diameter closest the distal end of the body and a radially extending back surface facing away from the distal end which forms an edge with the leading surface that is adapted to dig into the walls of the bore hole to lock the anchor in the bore hole.

13. A suture anchored to a hole in a bone comprising:
a length of suturing thread; and
a body having a tip on a leading end which is first inserted into the hole in the bone, said tip including a hole through which said length of suturing thread extends, at least one resilient wall forming a trailing portion of the body, said wall having a barb formed on an outer surface which faces the hole in the bone, said barb defining an edge that digs into the hole in the bone when tension is applied to the suturing thread.

14. The suture of claim 13 wherein two resilient walls are provided which are compressed together when the suture anchor is inserted into the hole in the bone, said two walls being separated by first and second longitudinal slots that extend from the tip to a trailing end of the body.

15. The suture of claim 14 wherein said suturing thread is reversely bent to form first and second leads extending from first and second ends of the hole in said tip with first and second leads of said suturing thread extending through the first and second slots, respectively, and out of the hole in the bone.

16. The suture of claim 14 wherein said first and second resilient walls are biased outwardly to cause said barbs to engage the wall of the hole in the bone wherein tension exerted on said suturing thread causes said resilient walls to diverge in an outwardly scissoring relationship to firmly anchor said body in the bone.

17. The suture of claim 14 wherein the first and second slots are diametrically opposed and the hole the first slot is formed to the side of the body in which the second slot is formed.

18. The suture of claim 13 wherein said tip is partially conical and terminates in a rounded end.

19. The suture of claim 13 wherein a plurality of barbs are provided.

20. The suture of claim 13 wherein said wall is semi-cylindrical in shape and said barb is generally arcuate and extends in a circumferential direction about said wall.

21. The suture of claim 20 wherein said barb has a frustoconical leading surface with a minimum diameter closest the leading end of the body and a radially extending back surface facing away from the leading end which forms an edge with the leading surface that is adapted to dig into the walls of the bore hole to lock the anchor in the bore hole.

22. A method of anchoring a suture in a bone with a suture anchor having a tip on a leading end, said tip including a hole through which a length of suturing thread extends, at least one resilient wall forming a trailing portion of the body, said wall having a barb formed on an outer surface which faces a wall of the hole in the bone, said barb defining an edge which is adapted to engage the wall of the hole in the bone, comprising the steps of:

forming a hole in the bone;

inserting said suture anchor to a desired depth in the hole in the bone with the tip being inserted first, the trailing portion following said tip, and the suturing thread extending from the hole in the tip and then along the length of said trailing portion and out of the hole in the bone; and pulling on the portion of suture material extending out of the hole and thereby urging the barb into firmer engagement with the wall of the hole in the bone.

23. The method of claim 22 wherein a plurality of resilient walls are provided and each of said resilient walls having a barb formed thereon, said method further comprising the step of scissoring said walls outwardly during said pulling step.

24. The method of claim 23 further comprising the step of scissoring the resilient walls together during the inserting step to fit the suture anchor into the hole in the bone.

25. The method of claim 22 wherein two resilient walls are provided which are separated by first and second longitudinal slots that extend from the tip to a trailing end of the body said method further comprising compressing said two walls together when the suture anchor is inserted into the hole in the bone.

26. The suture anchor of claim 25 further comprising the step of bending said suturing thread reversely to form first and second leads extending from first and second ends of the hole in said tip with first and second leads of said suturing thread extending through the first and second slots, respectively, and out of the hole in the bone.

* * * * *